(12) United States Patent
Nagano et al.

(10) Patent No.: US 7,753,966 B2
(45) Date of Patent: Jul. 13, 2010

(54) HAIR DYE STABILIZER

(75) Inventors: Junko Nagano, Kanagawa (JP); Kazuki Sugiyama, Kanagawa (JP); Kyoko Hirano, Kanagawa (JP); Kunihide Hoshino, Kanagawa (JP); Takashi Aida, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 12/440,624

(22) PCT Filed: Jul. 10, 2007

(86) PCT No.: PCT/JP2007/063749
§ 371 (c)(1),
(2), (4) Date: Mar. 10, 2009

(87) PCT Pub. No.: WO2008/035500
PCT Pub. Date: Mar. 27, 2008

(65) Prior Publication Data
US 2010/0011517 A1 Jan. 21, 2010

(30) Foreign Application Priority Data
Sep. 20, 2006 (JP) ............................. 2006-254956

(51) Int. Cl.
*A61Q 5/10* (2006.01)
(52) U.S. Cl. .................. 8/405; 8/406; 8/408; 8/561; 8/587; 8/617
(58) Field of Classification Search .............. 8/405, 8/408, 561, 587, 617
See application file for complete search history.

(56) References Cited

U.S. PATENT DOCUMENTS 4,961,925 A * 10/1990 Tsujino et al. ................. 8/406

FOREIGN PATENT DOCUMENTS

| | | |
|---|---|---|
| EP | 0 461 526 | 12/1991 |
| GB | 2 018 836 | 10/1979 |
| JP | 55-6570 | 1/1980 |
| JP | 4-46114 | 2/1992 |
| JP | 4-312515 | 11/1992 |
| JP | 6-172145 | 6/1994 |
| JP | 9-20627 | 1/1997 |
| JP | 9-315948 | 12/1997 |
| JP | 2000-344638 | 12/2000 |
| JP | 2003-137758 | 5/2003 |
| JP | 2005-162681 | 6/2005 |

* cited by examiner

*Primary Examiner*—Eisa B Elhilo
(74) *Attorney, Agent, or Firm*—Fitzpatrick, Cella, Harper & Scinto

(57) ABSTRACT

It is to provide a hair dye stabilizer capable of stably storing a readily oxidizable compound in a hair dye, especially an oxidizing dye intermediate or a coupler and effective for remarkably improving the offensive odor problem. Furthermore, it is to provide a hair dye stabilizer giving improvement in damage on the hair, hardly irritating the skin, and free from adverse effects on the dyeing ability of the hair dye.

As the active component constituting the hair dye stabilizer, a compound which is a mercapto-hydrocarbon compound and/or a thiol alcohol compound and does not contain a functional group reactive with a dye intermediate or a coupler is used. A readily oxidizable compound and the like in a hair dye can be stably stored by the use of an extremely small amount of the stabilizer.

6 Claims, 9 Drawing Sheets

Test Example 2 at 1 day

Test Example 2 at 4 days

Test Example 2 at 2 weeks

Example 3 (thioglycol) at 1 day

Example 3 (thioglycol) at 4 days

Example 3 (thioglycol) at 2 weeks

Example 4 (thiogeraniol) at 1 day

Example 4 (thiogeraniol) at 4 days

Example 4 (thiogeraniol) at 2 weeks

HAIR DYE STABILIZER

TECHNICAL FIELD

The present invention relates to a hair dye stabilizer comprising a specified mercapto-hydrocarbon compound and/or thiol alcohol compound as active component(s) and a fragrance composition comprising the hair dye stabilizer. Moreover, the invention relates to a resorcin and/or p-nitro-o-phenylenediamine-containing hair dye stabilizer comprising the above compound(s) as active component(s) and a fragrance composition comprising the hair dye stabilizer. Furthermore, the invention relates to a hair dye composition containing the above hair dye stabilizer or a hair dye composition containing the fragrance composition.

BACKGROUND ART

At the dyeing treatment of hair, it is most common to use a double preparation type oxidative hair dye comprising a first preparation containing a hair swelling agent such as ammonia and an oxidative dye intermediate and, if necessary, a coupler, and a second preparation containing an oxidizing agent such as hydrogen peroxide. The mechanism of hair dyeing in the double preparation type oxidative hair dye includes swelling of hair by the first preparation to permeate the oxidative dye intermediate, the coupler, and the like into the hair and subsequent oxidative polymerization of the oxidative dye intermediate and the like in the hair by the second preparation to develop a color, thereby hair dyeing being completed. The hair dyeing by this method is excellent in hair-dyeing ability and also can create a variety of color tones by blending various couplers for hair dyeing in combination with an oxidative dye intermediate and the like, so that the method is widely utilized.

Recently, in order to alleviate the damage of hair, a technology of using an oxidase instead of hydrogen peroxide to be used in the second preparation has been reported (see, e.g., Patent Document 1). Since the oxidase is used, single preparation type one wherein the second preparation is combined with the first preparation in the absence of oxygen becomes possible. Also, there has been utilized a single preparation type oxidative hair dye wherein an oxidative dye intermediate and the like undergo oxidative polymerization through uptake of oxygen in the air as an oxidizing agent after the application to hair.

However, a dye component in a hair dye base is high in reactivity, and therefore, there has been an inconvenience that, even at a stage in which the hair dye is stored before it is applied to hair, a polymerization occurs in the presence of oxygen in the air and thereby color is developed. Accordingly, various types of improvements for solving the above inconvenience have so far been made.

As one method, there may be mentioned a method of blocking the air from the hair dye. Namely, an improvement has been made such that the hair dye is produced or allowed to be a commercial product in an atmosphere in which the hair dye is hardly in contact with oxygen by removing oxygen dissolved in a base or by purging a container to which the base is stored with an inert gas which does not cause a reaction or the like. For example, there has been known a technology of conducting a mixing operation of components constituting a hair dye composition under an atmosphere having an oxygen concentration of 0.00015% or less (Patent Document 2). However, in order to perform such an operation, there still remains an inconvenience that suitable apparatus/equipments are required and hence economic burden for them is large.

Furthermore, since highly reactive dye compounds are still apt to be degenerated and the hair dyeing effect comes to be deteriorated with time, it is necessary to pay a considerable effort for maintaining the value as a commercial product.

In that respect, a method of using a chemical agent is economically advantageous and there is known a technology for preventing degeneration or the like of a highly reactive dye compound and inhibiting the deterioration of the hair dyeing effect over time by adding a reducing agent such as a bisulfate salt or vitamin C (ascorbic acid and a salt thereof) into the base to trap active species to be generated in the base.

Moreover, there has been known a technology of adding mercaptans such as thioglycolic acid, thiolactic acid, or mercaptosuccinic acid into a base to stabilize a dye compound (see, e.g., Patent Document 3, Patent Document 4, etc.). Although the method is effective to some extent, it still has not only a defect that the mercaptans used gives out a very strong offensive smell and thus makes an operator or the like unpleasant but also an inconvenience that the amount of the chemical agent to be used is large and thus it damages the hair and irritates the skin. Furthermore, in the case where mercaptans is applied to an actual commercial product, there sometimes arises a problem that it exerts an influence on the blending balance of an oxidative dye intermediate and a coupler, or the like.

In addition, a technology of incorporating an iron ion into mercaptans has been reported (Patent Document 5), but the above inconvenience is still not solved even in the technology. Moreover, a technology of utilizing a mercapto compound such as thioglycerol, thiolactic acid, thiomalic acid, or cysteamine as a polymerization inhibitor for oxidative dyes has been reported (Patent Document 6). However, these compounds are only listed in the specification but no specific effects are confirmed in Examples or the like.

Patent Document 1: JP-A-6-172145

Patent Document 2: JP-A-2000-344638

Patent Document 3: JP-A-55-6570

Patent Document 4: JP-A-4-312515

Patent Document 5: JP-A-9-315948

Patent Document 6: JP-A-2005-162681

DISCLOSURE OF THE INVENTION

Problems that the Invention is to Solve

Accordingly, it is an object of the invention to develop a hair dye stabilizer which enables stable storage of a readily oxidizable compound in a hair dye, particularly an oxidative dye intermediate, a coupler or the like and remarkably improves the problem of offensive smell. Another object is to develop a hair dye stabilizer giving improvement in damage on the hair, hardly irritating the skin, and free from adverse effects on the dyeing ability of the hair dye, in addition to the above characteristics.

Moreover, it is an object of the invention to provide a hair dye stabilizer which can stabilize the oxidative dye intermediate or the like by the use of an extremely small amount thereof, suppresses the damage of hair as far as possible, and reduces the influence of offensive smell.

Furthermore, it is another object to provide a method of blocking the air from the above hair dye and a stabilization technology of a hair dye utilizing the above hair dye stabilizer, i.e., a technology of placing a hair dye and a stabilizer in an amount necessary for stabilizing the hair dye in a sealed container.

Means for Solving the Problems

As a result of the extensive studies on the characteristics and the like of mercaptans in the case of the use as a hair dye stabilizer from various angles in order to solve the above problems, the present inventors have found that a compound which is mercaptans or thiol alcohol compound having a specified structure and does not contain a functional group reactive with a dye intermediate or a coupler surprisingly has extremely excellent characteristics.

Namely, for example, the inventors have obtained a finding that, in the case where mercaptans has a carboxylic group, for example, in the case of thioglycolic acid, the compound can contribute the stabilization of most of oxidative dye intermediates and couplers but rather promotes the deterioration in the case where the oxidative dye intermediate or coupler is resorcin and/or p-nitro-o-phenylenediamine.

Furthermore, in the case of the application to a hair dye product in which the above specified oxidative dye intermediate or coupler are blended, the inventors have obtained a finding that not only it becomes difficult to create a constant color tone at the use but also there arises an inconvenience that the color tone of the dyed hair becomes different depending on the timing of the use even when the same commercial products are used.

Moreover, in the case of thiogeraniol or the like to be used as a fragrance raw material, the inventors have obtained a finding that its odor intensity is extremely strong but the odor is not an unpleasant odor when the amount to be added is about 0.002% by weight or less based on the total weight of a hair dye including a base and it becomes possible to make the odor at the use of a commercial product comfortable. Based on these findings, the inventors have further continued the studies and finally accomplished the invention.

Namely, the invention lies on the following.

(1) A hair dye stabilizer comprising a compound which is a mercapto-hydrocarbon compound and/or a thiol alcohol compound and does not contain a functional group reactive with a dye intermediate or a coupler. In this regard, the hair dye stabilizer means a stabilizer for an unstable substance present in a hair dye, particularly a stabilizer for a readily oxidizable substance.

(2) The hair dye stabilizer according to the above (1), wherein the dye intermediate or coupler to be blended with a hair dye is resorcin and/or p-nitro-o-phenylenediamine.

(3) A fragrance composition for hair dye comprising the hair dye stabilizer according to the above (1) or (2).

(4) A hair dye comprising the hair dye stabilizer according to the above (1) or (2) or the fragrance composition for hair dye according to the above (3).

(5) The fragrance composition for hair dye according to the above (3) or the hair dye according to the above (4), wherein the content of the hair dye stabilizer according to the above (1) or (2) is $1 \times 10^{-9}\%$ by weight or more and less than 1% by weight based on a total weight of the hair dye including a base.

(6) A sealed container in which a mixture containing a given amount of the hair dye stabilizer according to the above (1) or (2) or the fragrance composition for hair dye according to the above (3) and a hair dye is placed.

ADVANTAGE OF THE INVENTION

By blending the stabilizer of the invention into a hair dye, the stability of readily oxidizable substances in a hair dye base is remarkably enhanced, so that a hair dye which does not undergo deterioration and degeneration over time can be provided. Furthermore, the stabilizer does not adversely affect the dyeing ability of the dye.

Particularly, many of mercapto-hydrocarbon compounds and/or thiol alcohol compounds are high in odor intensity but they are excellent in stabilizing effect even when the amount of the compounds used is extremely small, so that they are advantageous.

In the case of thiol alcohol compounds which do not contain any functional group reactive with a dye intermediate or a coupler, they can not only contribute to the stabilization of an oxidative dye intermediate or a coupler but also prevent the deterioration of a hair dye product without adversely affecting the product since they have relatively weak odor intensity as compared with mercapto-hydrocarbons.

Moreover, in the case of thiogeraniol or the like which is a mercapto-hydrocarbon and is used as a fragrance raw material, the odor intensity is extremely strong but it has not a malodor at a specified concentration. In the case of such a material, it becomes possible to make odor comfortable when a fragrance to be used in combination is suitably adjusted in conformity to the odor.

Figure 1:
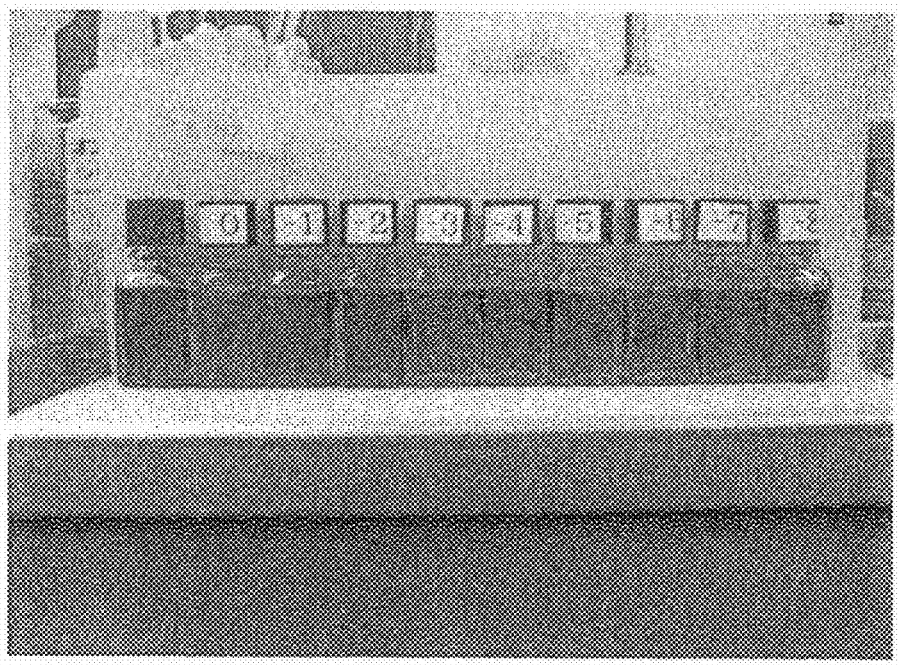
FIG. 1

The figure is a photograph illustrating amounts of thioglycerol added and change in color tone of a hair dye base first preparation immediately after the passage of one day.

FIG. 2

The figure is a photograph illustrating amounts of thioglycerol added and change in color tone of a hair dye base first preparation immediately after the passage of four days.

FIG. 3

The figure is a photograph illustrating amounts of thioglycerol added and change in color tone of a hair dye base first preparation immediately after the passage of two weeks.

FIG. 4

The figure is a photograph illustrating amounts of thioglycol added and change in color tone of a hair dye base first preparation immediately after the passage of one day.

FIG. 5

The figure is a photograph illustrating amounts of thioglycol added and change in color tone of a hair dye base first preparation immediately after the passage of four days.

FIG. 6

The figure is a photograph illustrating amounts of thioglycol added and change in color tone of a hair dye base first preparation immediately after the passage of two weeks.

FIG. 7

The figure is a photograph illustrating amounts of thiogeraniol added and change in color tone of a hair dye base first preparation immediately after the passage of one day.

FIG. 8

The figure is a photograph illustrating amounts of thiogeraniol added and change in color tone of a hair dye base first preparation immediately after the passage of four days.

FIG. 9

The figure is a photograph illustrating amounts of thiogeraniol added and change in color tone of a hair dye base first preparation immediately after the passage of two weeks.

BESET MODE FOR CARRYING OUT THE INVENTION

The following describes the present invention in detail.

The hair dye of the invention means a chemical agent or a chemical agent mixture to be used in dyeing hair of living organisms. Moreover, the hair dye of the invention includes not only a hair dye as a so-called quasi drug but also a hair dye as a cosmetic (hereinafter referred to as "hair dye"). Usually, the hair dye comprises an oxidative dye intermediate, a hair-swelling agent, an oxidizer, a surfactant, a higher alcohol, a hydrocarbon, a fragrance, other various compounding agents, and the like. Furthermore, as the preparation form, a double preparation type and a single preparation type are known.

The hair dye stabilizer referred to in the invention means a stabilizer for a hair dye and is effective for stabilizing substances which lacks stability and is present in the above hair dye, particularly effective for stabilizing a dye intermediate or a coupler present in the hair dye.

The mercapto-hydrocarbon compound referred to in the invention means a compound which contains a thiol group in the molecule, does not contain functional group reactive with the dye intermediate or the coupler, and is effective for stabilization of the hair dye.

Similarly, the thiol alcohols referred to in the invention is a compound which contains a thiol group and a hydroxyl group in the molecule and does not contain functional group reactive with the dye intermediate or the coupler, and is effective for stabilization of the hair dye.

The above functional group reactive with the dye intermediate and the coupler means a functional group reactive with the functional group possessed by the dye intermediate or the coupler and specifically, examples thereof include a carboxyl group and an amino group.

As the above mercapto-hydrocarbon compound, it is desired to use a compound having a large molecular weight and exhibiting little malodors and it is also desired to use a thiol compound which is a raw material for a specified fragrance. As preferred examples, there may be, for example, mentioned thiol compounds having a structure which does not contain a functional group reactive with the dye intermediate or the coupler and contains a ring having 5 or more carbon atoms which may contain a heteroatom, and thiol compounds having a linear chain having 6 or more carbon atoms. As more preferred examples, there may be mentioned thiol compounds having a structure which does not contain a functional group reactive with the dye intermediate or the coupler and contains a ring having 5 to 10 carbon atoms which may contain a heteroatom, and thiol compounds having an unsaturated group and having a linear chain having 8 to 12 carbon atoms.

Specifically, examples thereof include limonenthiol, thiogeraniol, thiomenthol, thioglycerin, p-menthen-8-thiol, 8-mercaptomenthone, and the like. As preferred examples of the above thiol alcohols, there may be, for example, mentioned thioglycol (2-mercaptoethanol), thioglycerol (2-mercapto-1,2-propanediol), and the like. Among them, thioglycerol is particularly preferred.

In this connection, when the compound has a carboxyl group or an amino group as a functional group like thioglycolic acid and thiolactic acid or cystine, the compound reacts with the dye intermediate or the coupler owing to the presence of these functional groups, so that the compound is not desirable. Furthermore, the compound having an ester bond or an aldehyde group is not desirable since it cannot stably exist in a hair dye base for a long period of time.

Although the amount of the above mercapto-hydrocarbon compound and/or thiol alcohol compound (hereinafter sometimes referred to as "thiol compound") to be blended varies depending on the type of the compounds present in the hair dye, it is sufficient to use in a small amount and usually, it is sufficient to use 1% by weight or less based on the total weight of the hair dye including the base. The lower limit amount also varies depending on the types of the compounds present in the hair dye but it is effective even in an amount of $1 \times 10^{-9}$% by weight. In this connection, the smaller amount of the compound to be added is more advantageous in view of odor.

The amount of the thiol compound to be blended is usually 1 to $1 \times 10^{-9}$% by weight, preferably 0.1 to $1 \times 10^{-8}$% by weight, and further preferably 0.02 to $1 \times 10^{-8}$% by weight based on the total weight of the hair dye including the base.

The amount of the mercapto compound to be blended is usually 1 to $1 \times 10^{-9}$% by weight, preferably 0.01 to $1 \times 10^{-8}$% by weight, and further preferably 0.002 to $1 \times 10^{-8}$% by weight based on the total weight of the hair dye including the base.

When the amount goes out of the above ranges, the odor of the thiol compound becomes apparent and the stability effect cannot fully be attained. Moreover, the above compound may be used solely but may be a mixture of two or more kinds thereof in any ratio.

The above thiol compounds can be easily available by purchase of commercial products or chemical synthesis according to usual methods.

The stabilization mechanism of the thiol compounds of the invention is not completely confirmed but the stabilization is attributable to trapping of atomic active oxygen and subsequent occurrence of a reaction of changing the thiol into a disulfide to form one molecule of water.

The dye intermediate to be used in the hair dye is not particularly limited so far as it is a known one but specifically, as the oxidative dye intermediate, there may be, for example, exemplified p-phenylenediamines, p-toluylenediamines, aminophenols, aminonitrophenols, diphenylamines, diaminophenylamines, N-phenylphenylenediamines, diaminopyridines, and the like as well as salts thereof.

The coupler to be used in the hair dye is not particularly limited so far as it is a known one but specifically, there may be, for example, exemplified 2,4-diaminophenoxyethanol hydrochloride, m-phenylenediamine hydrochloride, 2,6-diaminopyridine, 1,5-dihydroxynaphthalene, 5-(2-hydroxyethylamino)-2-methylphenol, m-aminophenol, m-phenylenediamine, m-aminophenol sulfate, m-phenylenediamine sulfate, catechol, α-naphthol, hydroquinone, pyrogallol, fluoroglycine, gallic acid, resorcin, and the like.

The amount of the above dye intermediate and coupler to be blended is not particularly limited but usually, preferably about 2 to 20% by weight based on the amount of the hair dye first preparation. In the case of the single component type hair dye, the amount is also preferably about 2 to 20% by weight based on the amount of the hair dye.

A hair dye composition containing the above hair dye stabilizer as one component of a hair dye belongs to the invention and it is also possible to form a fragrance composition for hair dye by blending a fragrance or an essential oil with the above hair dye stabilizer. The fragrance or essential oil to be used is not particularly limited but, since an alkali or an acid is used in a hair dye, it is necessary to use a stable fragrance or essential oil which is not affected by the chemical agent.

For example, the following fragrances or essential oils may be exemplified without limitation thereto. It is at least one kind of compound or essential oil selected from acetyl diisoamylene, linalool oxide, rosephenone, 2-methyl-4-(2,2,3-trimethyl-3-cyclopenten-1-yl)-2-buten-1-ol, 3-methyl-5-(2, 2,3-trimethyl-3-cyclopenten-1-yl)-pentan-2-ol, 2-ethyl-4-(2, 2,3-trimethyl-3-cyclopenten-1-yl)-2-buten-1-ol, 4-(1-ethoxyvinyl)-3,3,5,5-tetramethylcyclohexanone, cis-p-menthan-7-ol, nerolidol, raspberry ketone, α,3,3-trimethylcyclohexanemethyl formate, p-methoxyphenethyl alcohol, 2,2,6-trimethylcyclohexanecarboxylic acid ethyl ester, 2,6,6-trimethyl-1-crotonylcyclohexane, p-cymene, terpinolene, myrcene, heptanal, octanal, benzaldehyde, salicylic aldehyde, citronellal, α-hexylcinnamic aldehyde, methyl jasmonate, γ-nonyllactone, γ-decalactone, coumarin, anisole, p-cresyl methyl ether, β-naphthol methyl ether, β-naphthol ethyl ether, menthone, acetophenone, α-damascone, β-damascone, α-ionone, β-ionone, methyl ionone, irone, dihydrojasmone, cis-3-hexenol, heptanol, 2-octanol, benzyl alcohol, citronellol, geraniol, terpineol, tetrahydrogeraniol, anise alcohol, phenethyl alcohol, tansy oil, and basil oil. It may be a mixture of two or more thereof.

The amount of the above fragrance or essential oil to be blended is desirably 0.01 to 30% by weight, particularly 0.1 to 1.0% by weight in the hair dye.

Many thiol compounds have high odor intensity. Thus, in the invention, it is preferred to adopt the following method. Namely, in the distribution process of shipping from a factory and arriving at a consumer, there is no room for contamination of oxygen into a hair dye placed in a sealed container, so that it is unnecessary to question the deterioration of the dye through oxidation during the process. Only during the step of preparing a hair dye to a step of placing the hair dye into a sealed container, and a period of time for removing active gases such as air mixed into the hair dye at that time, the prevention of oxidative deterioration of the hair dye should be appropriately achieved.

Specifically, the amount of the thiol compound to be consumed by the base is actually measured beforehand and is comprehended as a basic data. Then, it is appropriate to realize such a situation that the thiol compound is present in a sealed container in an amount corresponding to the amount of the hair dye base present in the sealed container. When the amount of the thiol compound to be consumed by the base is actually measured, the numerical value can be easily found. The thiol compound may be added into the container in that amount but usually, a little larger amount than the amount is added. For example, it is desirable to add an additional amount thereof, which is about 5% by weight or less of that amount.

Herein, the sealed container means a container for placing a substance which dislikes the presence of oxygen and also means a container comprising a structure or material wherein oxygen gas hardly intrudes from the mouth of the container or the wall constituting the container. Any container for placing a hair dye can be used.

As preparation forms of the hair dye in the invention, there may be, for example, mentioned stick types, spray types, aerosol types, cream types, liquid types, and gel types, and the like. The hair dye stabilizer of the invention can be applied to all these preparation forms but, among them, the cream types and the liquid types are effective and, in particular, the liquid types having fluidity are effective.

Various kinds of compounding agents are used for hair dyes. A large number of compounding agents are known and the compounding agents can be suitably used in the invention. As representative compounding agents, there may be, for example, exemplified hair-swelling agents such as ammonia, nonionic surfactants, anionic surfactants, cationic surfactants, amphoteric surfactants, higher alcohols, hydrocarbons, fatty acids, waxes, thickeners, oils and fats, salts such as ammonium chloride, sodium chloride, potassium chloride, sodium carbonate, and sodium hydrogen carbonate, solvents, excipients, pH adjustors, aerosol propellants such as liquefied petroleum gas, dimethyl ether, and carbon dioxide, fragrances, various pilatory components, phosphoric acid, and conventional stabilizers other than the above, such as condensed phosphoric acid and salts thereof.

Example 1

The following describes the present invention further in detail with reference to Examples, but the invention is not restricted by these Examples. Incidentally, "%" or "part(s)" in numerals means "% by weight" or "part(s) by weight" unless otherwise specified.

Example 1

50 g of a liquid hair dye base (Bigen Speedy Color, manufactured by Hoyu Co. Ltd.) was weighed into a separable flask, and 0.1 g of thioglycerol was added. After the above separable flask was purged with nitrogen gas, the whole was stirred under a flow of nitrogen gas. After the resultant was divided into 40 g each in a 100 ml shampoo bottle and purging with nitrogen gas was performed, the bottle was capped, thereby a liquid hair dye base first preparation being prepared.

Test Example 1

The liquid hair dye base first preparation of Example 1 was stored in a constant-temperature tank set at room temperature or 40° C. for 30 days. This first preparation was used as a sample.

(Extraction of Remaining Dyes from Liquid Hair Dye Base First Preparation)

About 4 g of an acetonitrile solution containing 500 ppm of benzonitrile was placed in a 10 mL sample vial and then the amount was accurately measured. About 0.2 g of the above sample was added thereto and the amount was accurately measured, followed by thorough mixing. The liquid in the sample vial was sucked by means of a syringe and was placed in a vial under filtration. Then, it was analyzed by means of a column ODS-80A in high performance liquid chromatography (HP 1100 manufactured by Hewlett-Packard Company) to measure amounts of remaining dyes in the sample. The results are shown in Table 1.

Comparative Example 1

A liquid hair dye base first preparation was prepared by performing the same operations as in Example 1 except that thioglycolic acid was used instead of thioglycerol. The liquid hair dye base first preparation of Comparative Example 1 was treated as in Example 1 to perform a stability test. The results are shown in Table 1.

TABLE 1

|  | Example 1 (%) | Comparative Example 1 (%) 40° C. | Control | Example 1 (%) | Comparative Example 1 (%) room temperature | Control |
| --- | --- | --- | --- | --- | --- | --- |
| m-Aminophenol | 1.59 | 0.82 | 1 | 1.09 | 1.00 | 1 |
| p-Nitro-o-phenylenediamine | 1.19 | 0.31 | 1 | 1.02 | 0.51 | 1 |
| Resorcinol | 1.29 | 0.61 | 1 | 1.10 | 0.85 | 1 |

In this connection, neither thioglycerol nor thioglycolic acid was added in Control. Moreover, the numerals in the table were relative values when the values in Control were regarded as 1.

Example 2

40 g of a liquid hair dye base first preparation obtained by adding thioglycerol to a liquid hair dye base (Bigen Speedy Color, manufactured by Hoyu Co. Ltd.) in an amount adjusted as shown in Table 2 was placed in a 100 ml shampoo bottle and, after purging with nitrogen gas was performed, the bottle was capped and stored at room temperature.

Test Example 2

Immediately after the passage of a given period of storage time of the shampoo bottle in which the above liquid hair dye base first preparation was placed, the color tone of the liquid hair dye base first preparation was visually observed by three panelists. The results are shown in Table 2. The color tones in the table show the color tones of the results observed by the largest number of the panelists (the same shall apply hereinafter). Moreover, photographs of change in color tone of the hair dye base first preparation immediately after the passage of the above given period are shown in FIG. 1 to FIG. 3.

Figure 2:
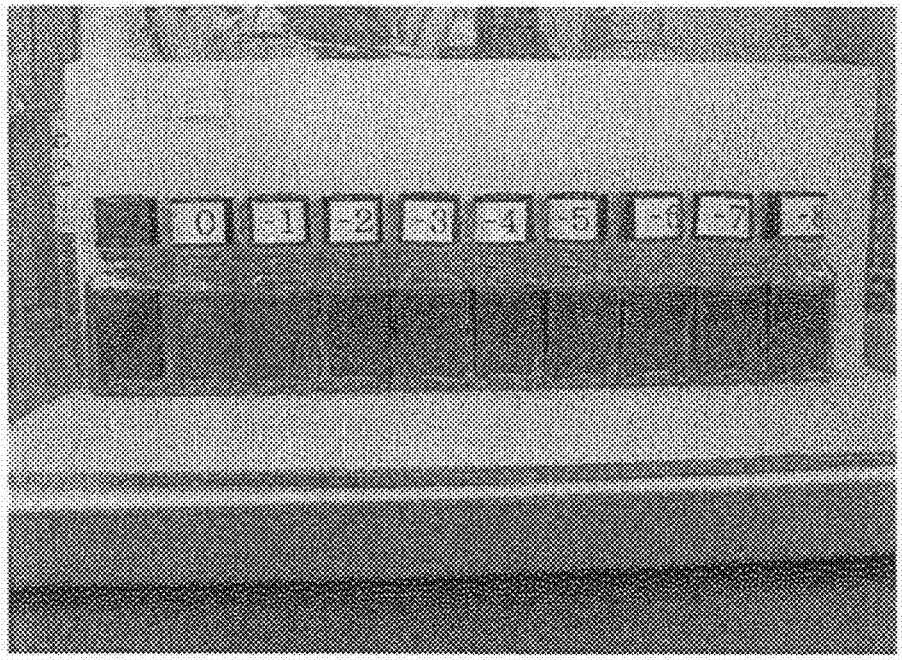
Figure 3:
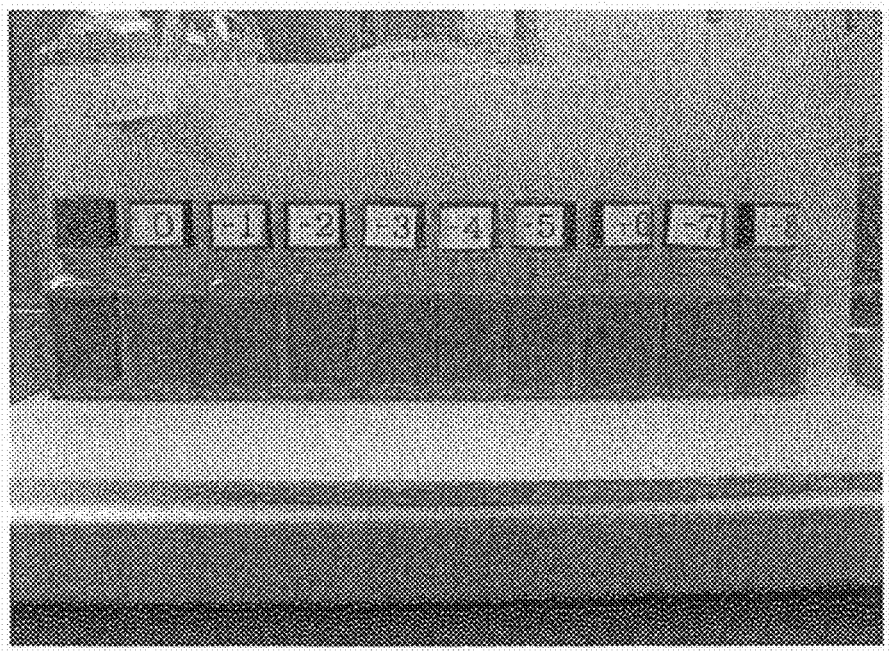

FIG. 1 to FIG. 3 are photographs in full color. In each photograph, there was photographed an appearance where nine shampoo bottles to which numbers 0 to 8 were assigned and one shampoo bottle as a blank on the left most were arranged in a single row. FIG. 1 shows the shampoo bottles immediately after the passage of one day (1 day), FIG. 2 shows the bottles immediately after the passage of four day (4 days), and FIG. 3 shows the bottles immediately after the passage of two weeks (2 weeks). The same shall apply in FIG. 4 to FIG. 6 and FIG. 7 to FIG. 9.

In full-color photographs, the above change in color tone was clear and could be instantaneously judged. From the photographs, when the liquid hair dye base first preparation was stored at room temperature for 2 weeks, it was revealed that a stabilization effect was shown even at a thioglycerol concentration of 0.0001 ppm. In this regard, since the photographs are monochrome ones in the present specification, the above change in color tone is not clear and thus is difficult to judge. The same shall apply in FIG. 4 to FIG. 6 and FIG. 7 to FIG. 9.

TABLE 2

|  |  | Sample number | | | | | | | | |
| --- | --- | --- | --- | --- | --- | --- | --- | --- | --- | --- |
|  |  | 0 | 1 | 2 | 3 | 4 | 5 | 6 | 7 | 8 |
|  | Amount of thioglycerol added (%) | 1 | 0.1 | 0.01 | 0.001 | 0.0001 | 0.00001 |  |  |  |
|  | Amount of thioglycerol added (ppm) | 10000 | 1000 | 100 | 10 | 1 | 0.1 | 0.01 | 0.001 | 0.0001 |
| Color tone | 1 Day | orange | brown | black | black | black | black | black | black | black |
|  | 4 Days | orange | orange | black | black | black | black | black | black | black |
|  | 2 Weeks | orange | orange | dark orange | dark orange | dark orange | dark orange | dark orange | dark orange | dark orange |

In Control, the bottles showed black in all cases after 1 Day, 4 Days, and 2 Weeks. In this connection, thioglycerol was not added in Control.

Example 3

Thioglycol was added to a liquid hair dye base (Bigen Speedy Color, manufactured by Hoyu Co. Ltd.) in an amount adjusted as shown in Table 3 and then, the same operations as in Example 2 were performed to store a shampoo bottle in which the above liquid hair dye base first preparation was placed. Immediately after the passage of a given period of storage time of the shampoo bottle in which the above liquid hair dye base first preparation was placed, the same operations as in Test Example 2 were performed and the color tone of the liquid hair dye base first preparation was visually observed by three panelists. The results are shown in Table 3.

Figure 4:
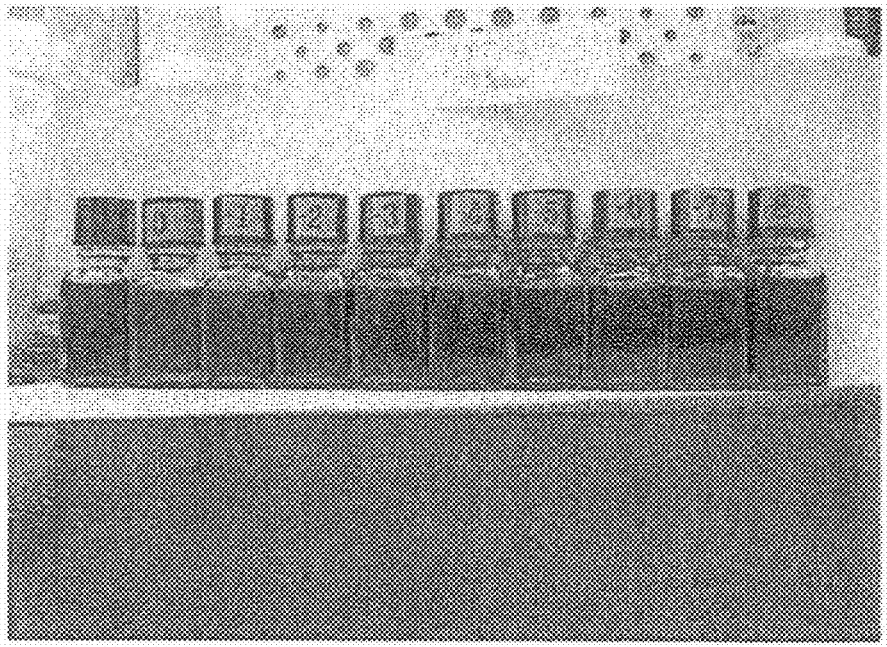
Figure 5:
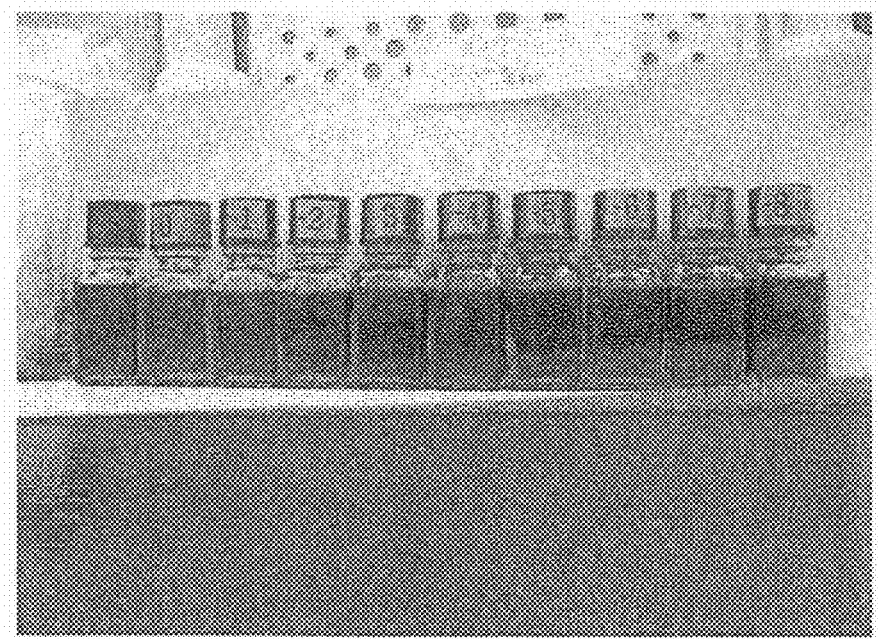
Figure 6:

Moreover, photographs of change in color tone of the liquid hair dye base first preparation are shown in FIG. 4 to FIG. 6. FIG. 4 to FIG. 6 are photographs in full color and the above change in color tone was clear and could be instantaneously judged. From the photographs, when the liquid hair dye base first preparation was stored at room temperature for 2 weeks, it was revealed that a stabilization effect was shown even at a thioglycol concentration of 0.0001 ppm. In this regard, since the photographs are monochrome ones in the present specification, the above change in color tone is not clear and thus is difficult to judge.

TABLE 3

| | Sample number | | | | | | | | |
|---|---|---|---|---|---|---|---|---|---|
| | 0 | 1 | 2 | 3 | 4 | 5 | 6 | 7 | 8 |
| Amount of thioglycol added (%) | 1 | 0.1 | 0.01 | 0.001 | 0.0001 | 0.00001 | | | |
| Amount of thioglycol added (ppm) | 10000 | 1000 | 100 | 10 | 1 | 0.1 | 0.01 | 0.001 | 0.0001 |
| Color tone 1 Day | orange | brown | black | black | black | black | black | black | black |
| 4 Days | orange | orange | black brown | black brown | black brown | black brown | black brown | black brown | black brown |
| 2 Weeks | orange | orange | brown | brown | brown | brown | brown | brown | brown |

In Control, the bottles showed black in all cases after 1 Day, 4 Days, and 2 Weeks. In this connection, thioglycol was not added in Control.

Example 4

Figure 7:
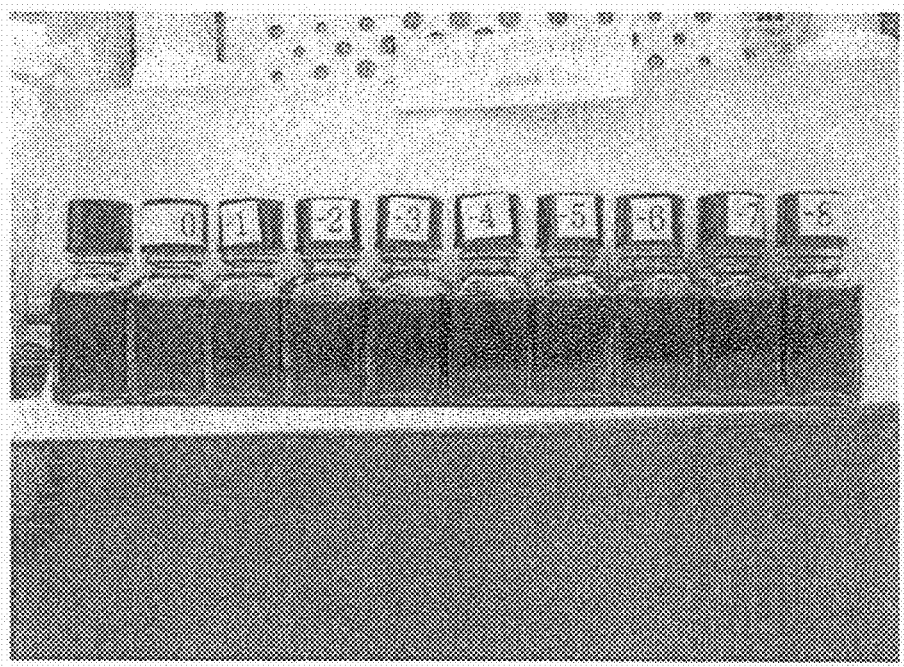
Figure 8:
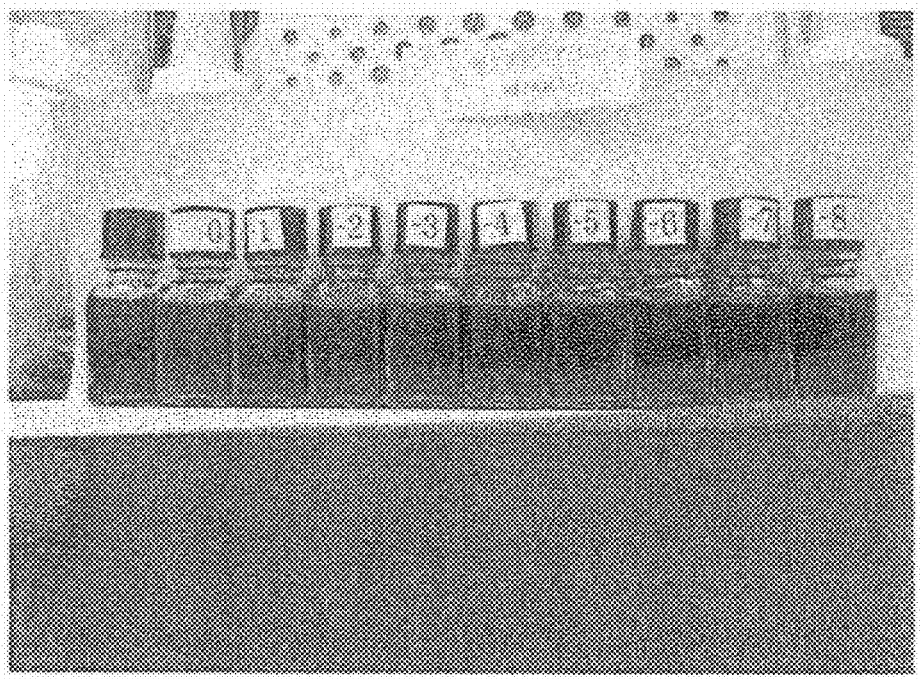
Figure 9:
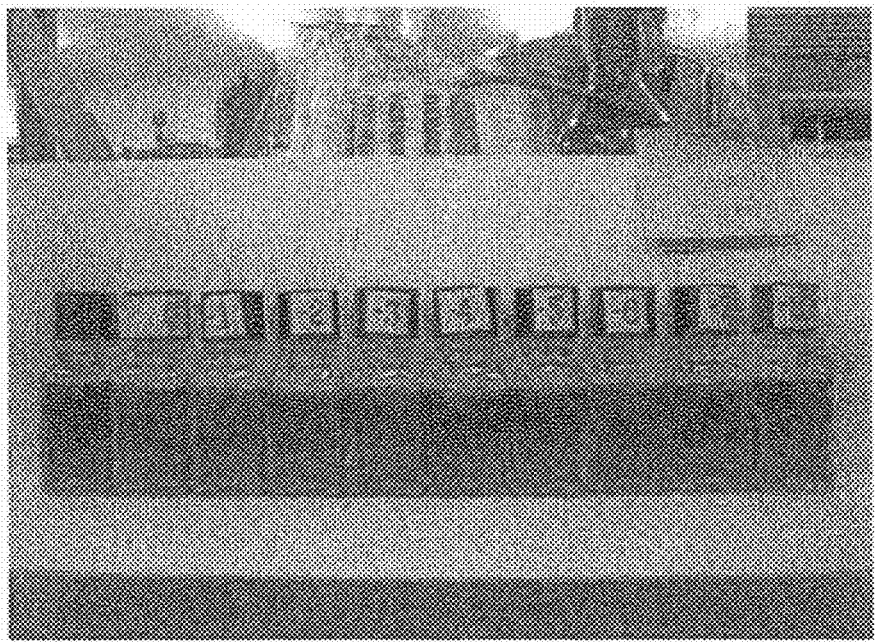

Thiogeraniol was added to a liquid hair dye base (Bigen Speedy Color, manufactured by Hoyu Co. Ltd.) in an amount adjusted as shown in Table 4 and then, the same operations as in Example 2 were performed to store a shampoo bottle in which the above liquid hair dye base first preparation was placed. Immediately after the passage of a given period of storage time of the shampoo bottle in which the above liquid hair dye base first preparation was placed, the same operations as in Test Example 2 were performed and the color tone of the liquid hair dye base first preparation was visually observed by three panelists. The results are shown in Table 4. Moreover, photographs of change in color tone of the liquid hair dye base first preparation are shown in FIG. 7 to FIG. 9. FIG. 7 to FIG. 9 are photographs in full color and the above change in color tone was clear and could be instantaneously judged. From the photographs, when the liquid hair dye base first preparation was stored at room temperature for 2 weeks, it was revealed that a stabilization effect was shown even at a thiogeraniol concentration of 0.0001 ppm. In this regard, since the photographs are monochrome ones in the present specification, the above change in color tone is not clear and thus is difficult to judge.

In Control, the bottles showed black in all cases after 1 Day, 4 Days, and 2 Weeks. In this connection, thiogeraniol was not added in Control. In this Example, (E)-3,7-dimethyl-2,6-octadien-1-thiol was used as thiogeraniol.

Example 5

Each of the compounds shown in Table 5 was added to a liquid hair dye base (Bigen Speedy Color, manufactured by Hoyu Co. Ltd.) in an amount adjusted as shown in Table 5 and then, the same operations as in Example 2 were performed to obtain a shampoo bottle in which the above liquid hair dye base first preparation was placed. The cap of the shampoo bottle was opened and the odor of the compounds shown in Table 5 was evaluated by a sensory test based on the following evaluation criteria, which was performed by five special panelists. The results are shown in Table 5.

(Evaluation Criteria)

C: odor is felt

B: odor is slightly felt

A: odor is hardly felt

TABLE 4

| | Sample number | | | | | | | | |
|---|---|---|---|---|---|---|---|---|---|
| | 0 | 1 | 2 | 3 | 4 | 5 | 6 | 7 | 8 |
| Amount of thiogeraniol added (%) | 1 | 0.1 | 0.01 | 0.001 | 0.0001 | 0.00001 | | | |
| Amount of thiogeraniol added (ppm) | 10000 | 1000 | 100 | 10 | 1 | 0.1 | 0.01 | 0.001 | 0.0001 |
| Color tone 1 Day | orange | brown | black | black | black | black | black | black | black |
| 4 Days | orange | black brown | black brown | black brown | black brown | black brown | black brown | black brown | black brown |
| 2 Weeks | orange | brown | brown | brown | brown | brown | brown | brown | brown |

TABLE 5

| | Amount added (%) | | | | | | | | |
|---|---|---|---|---|---|---|---|---|---|
| | 1 | 0.1 | 0.08 | 0.05 | 0.02 | 0.01 | 0.001 | 0.0001 | 0.00001 |
| Thioglycerol | C | B | A | A | A | A | A | A | A |
| Thioglycol | C | C | C | B | A | A | A | A | A |

Example 6

Each of the compounds shown in Table 6 was added to a liquid hair dye base (Bigen Speedy Color, manufactured by Hoyu Co. Ltd.) in an amount adjusted as shown in Table 6 and then, the same operations as in Example 2 were performed to obtain a shampoo bottle in which the above liquid hair dye base first preparation was placed. The cap of the shampoo bottle was opened and the odor of the compounds shown in Table 6 was evaluated by a sensory test in the same manner as in Example 5. The results are shown in Table 6.

TABLE 6

| | Amount added (%) | | | | | | | |
|---|---|---|---|---|---|---|---|---|
| | 0.1 | 0.01 | 0.008 | 0.005 | 0.002 | 0.001 | 0.0001 | 0.00001 |
| Limonenethiol | C | C | C | C | B | A | A | A |
| Thiogeraniol | C | C | C | C | B | A | A | A |
| 8-Mercaptomenthone | C | B | A | A | A | A | A | A |

In Example 6, (E)-3,7-dimethyl-2,6-octadien-1-thiol was used as thiogeraniol.

While the invention has been described in detail and with reference to specific embodiments thereof, it will be apparent to one skilled in the art that various changes and modifications can be made therein without departing from the spirit and scope thereof. The present application is based on Japanese Patent Application No. 2006-254956 filed on Sep. 20, 2006, and the contents are incorporated herein by reference.

The invention claimed is:

1. A hair dye composition comprising (i) a stabilizer comprising as an active component limonenthiol, thiogeraniol, thiomenthol, thioglycerin, p-menthen-8-thiol, 8-mercaptomenthone, thioglycol or thioglycerin and (ii) a dye intermediate or coupler comprising resorcin or p-nitro-o-phenylenediamine, wherein said stabilizer does not contain a functional group reactive with said dye intermediate or a coupler.

2. A hair dye composition according to claim 1 comprising a fragrance component.

3. The hair dye composition according to claim 1, wherein the hair dye stabilizer is from $1 \times 10^{-9}$ up to 1% by weight of said composition.

4. A sealed container comprising the hair dye composition according to claim 1.

5. The hair dye according to claim 2, wherein the hair dye stabilizer is from $1 \times 10^{-9}$ up to 1% by weight of said composition.

6. A sealed container comprising the hair dye composition according to claim 2.

* * * * *